(12) United States Patent
Rachwal et al.

(10) Patent No.: US 11,970,641 B2
(45) Date of Patent: Apr. 30, 2024

(54) IONIC COMPOSITIONS AND RELATED USES THEREOF

(71) Applicant: NITTO DENKO CORPORATION, Osaka (JP)

(72) Inventors: Stanislaw Rachwal, Oceanside, CA (US); Yufen Hu, San Diego, CA (US); Hongxi Zhang, Temecula, CA (US)

(*) Notice: Subject to any disclaimer, the term of this patent is extended or adjusted under 35 U.S.C. 154(b) by 899 days.

(21) Appl. No.: 16/490,487

(22) PCT Filed: Mar. 2, 2018

(86) PCT No.: PCT/US2018/020754
§ 371 (c)(1),
(2) Date: Aug. 30, 2019

(87) PCT Pub. No.: WO2018/161025
PCT Pub. Date: Sep. 7, 2018

(65) Prior Publication Data
US 2020/0071581 A1   Mar. 5, 2020

Related U.S. Application Data

(60) Provisional application No. 62/466,112, filed on Mar. 2, 2017.

(51) Int. Cl.
| C09J 201/00 | (2006.01) |
| C08K 3/30 | (2006.01) |
| C08K 5/3472 | (2006.01) |

(52) U.S. Cl.
CPC ........... *C09J 201/00* (2013.01); *C08K 3/30* (2013.01); *C08K 5/3472* (2013.01); *C09J 2203/326* (2013.01); *C09J 2301/408* (2020.08)

(58) Field of Classification Search
None
See application file for complete search history.

(56) References Cited

U.S. PATENT DOCUMENTS

| 4,483,835 A | 11/1984 | Zones |
| 6,471,939 B1 | 10/2002 | Boix et al. |
| 6,620,308 B2 | 9/2003 | Gilbert |
| 7,208,605 B2 | 4/2007 | Davis, Jr. et al. |
| 7,208,606 B2 | 4/2007 | Drent et al. |
| 7,332,218 B1 | 2/2008 | Gilbert |

(Continued)

FOREIGN PATENT DOCUMENTS

| CN | 104450020 A | * 3/2015 |
| EP | 2158077 A1 | 3/2010 |

(Continued)

OTHER PUBLICATIONS

JP-2011017000-A, Jan. 2011, machine translation (Year: 2011).*

(Continued)

*Primary Examiner* — Satya B Sastri
(74) *Attorney, Agent, or Firm* — Maschoff Brennan; David W. Old; Yuefen Zhou

(57) ABSTRACT

The present disclosure generally relates to ionic compositions which may be used in or as an adhesive material for selectively adhering two items together. More particularly, but not exclusively, the present disclosure relates to ionic compositions that include a cationic imidazolium compound and an anionic compound such as a sulfonyl imide compound.

3 Claims, 2 Drawing Sheets

(56) References Cited

U.S. PATENT DOCUMENTS

| | | | |
|---|---|---|---|
| 7,465,492 B2 | 12/2008 | Gilbert | |
| 7,901,812 B2 | 3/2011 | Michot et al. | |
| 7,968,188 B2 | 6/2011 | Gilbert | |
| 8,134,027 B2 | 3/2012 | Okumura et al. | |
| 8,916,267 B2 | 12/2014 | Bauer et al. | |
| 2010/0298466 A1 | 11/2010 | Schwind et al. | |
| 2014/0030515 A1* | 1/2014 | Morimoto | C09J 7/385 524/106 |
| 2015/0105596 A1 | 4/2015 | Wang et al. | |
| 2015/0279577 A1 | 10/2015 | Uchida et al. | |
| 2016/0009962 A1 | 1/2016 | Yamada et al. | |
| 2017/0015814 A1* | 1/2017 | Ishizaki | C09J 135/04 |
| 2017/0355892 A1 | 12/2017 | Heucher et al. | |

FOREIGN PATENT DOCUMENTS

| | | | | |
|---|---|---|---|---|
| EP | 2690149 A1 | | 1/2014 | |
| JP | 2004-530619 A | | 10/2004 | |
| JP | 2010037354 A | | 2/2010 | |
| JP | 2010037355 A | | 2/2010 | |
| JP | 2011-016990 A | | 1/2011 | |
| JP | 2011017000 A | * | 1/2011 | C09J 133/04 |
| JP | 2011052056 A | | 3/2011 | |
| JP | 2011-129400 A | | 6/2011 | |
| JP | 2012116802 A | | 6/2012 | |
| JP | 2014189671 A | | 10/2014 | |
| JP | 6017217 B2 | | 10/2016 | |
| KR | 20100067171 A | * | 6/2010 | |
| KR | 20140014004 A | | 2/2014 | |
| TW | 201006897 A | | 2/2010 | |
| TW | 201406897 A | | 7/2013 | |
| TW | 201641652 A | | 12/2016 | |
| WO | 2008150228 A1 | | 12/2008 | |
| WO | WO-2009084651 A1 | * | 7/2009 | C09J 11/06 |
| WO | 2016135341 A1 | | 9/2016 | |
| WO | 2016136924 A1 | | 9/2016 | |
| WO | WO-2017064918 A1 | * | 4/2017 | C08K 5/0075 |

OTHER PUBLICATIONS

WO-2009084651-A1, Feb. 2009, Machine translation (Year: 2009).*
CN 104450020 A, Mar. 2015 (Year: 2015).*
KR 20100067171 A, Jun. 2010, Machine translation (Year: 2010).*
WO2017/064918 A1, Apr. 2017, machine translation (Year: 2017).*
Office Action in corresponding Chinese application, 201880028136.X, dated Sep. 16, 2020; English machine translation also attached.
Office Action in corresponding Chinese application, 201880028136.X, dated Apr. 9, 2021; English machine translation also attached.
Office Action in corresponding Japanese application, 2019-547402, dated Aug. 24, 2021; English machine translation also attached.
Office Action in corresponding Taiwanese application, 107107145, dated Sep. 24, 2021; English machine translation also attached.
Office Action in corresponding Japanese application, 2019-547402, dated Feb. 15, 2022; English machine translation also attached.
Registry (STN) [online], 1996 Registration No. 174908-40-8.
Kückmann et al., Rhenium (V) Oxo Complexes with N-Heterocyclic Carbenes, Inorganic Chemistry, vol. 43. No. 22, pp. 7068-7074, Nov. 2004.
Leijonmarck, S. et al., Electrochemical Characterization of Electrically Induced Adhesive Debonding, Journal of the Electrochemical Society, 2011, 158(10), p. 109-p. 114.
Gatty, H.K. et al., Temporary Wafer Bonding and Debonding for 3D Integration Using an Electrochemically Active Polymer Adhesive, ECS Journal of Solid State Science and Technology, 2014, 3(5), p. 115-p. 121.
International Search Report and Written Opinion, PCT/US2018/020754, dated Jun. 4, 2018.
Office Action in corresponding Korean application, 10-2019-7028858 issued Apr. 17, 2022, English translation is attached.
Office Action in corresponding Taiwanese application, 107107145 issued Apr. 8, 2022, English translation is attached.

* cited by examiner

IONIC COMPOSITIONS AND RELATED USES THEREOF

CROSS-REFERENCE TO RELATED APPLICATIONS

This application is a national phase application of PCT/US2018/020754, filed on Mar. 2, 2018, which claims the benefit of U.S. Provisional Patent Application No. 62/466,112, filed Mar. 2, 2017, the content of which is incorporated by reference in its entirety.

BACKGROUND

The present disclosure generally relates to ionic compositions which may be used in or as an adhesive material for selectively adhering two items together. More particularly, but not exclusively, the present disclosure relates to ionic compositions that include a cationic imidazolium compound and an anionic compound such as a sulfonyl imide compound.

Certain compositions are known which may be used as an adhesive coating that is applied to an electrically conductive surface of a first substrate. The adhesive coating may be sandwiched between the electrically conductive surface of the first substrate and an electrically conductive surface of a second substrate in order to adhere or join the first and second substrates together. Upon the application of an electric potential, the adhesive coating is de-bonded from one or both of the first and second substrates in order to separate the first and second substrates from one another. It has been observed however that certain forms of this type of coating may have an undesired corrosive effect on the electrically conductive surfaces to which they are applied. Thus, there remains a need for further contributions in this area of technology.

The subject matter disclosed and claimed herein is not limited to embodiments that solve any disadvantages or that operate only in environments such as those described above. Rather, this background is only provided to illustrate examples of where the present disclosure may be utilized.

SUMMARY

The present disclosure generally relates to ionic compositions which may be used in or as an adhesive material for selectively adhering two items together. More particularly, but not exclusively, the present disclosure relates to ionic compositions that include a cationic imidazolium compound and an anionic compound such as an anionic sulfonyl imide compound.

In one embodiment, a composition includes a cationic compound according to Formula (I):

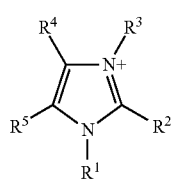

Formula (I)

wherein $R^1$ represents a $C_1$-$C_8$ alkyl, a $C_1$-$C_8$ hydroxyalkyl, a $C_1$-$C_8$ alkenyl, or a $C_1$-$C_8$ alkoxyalkyl, $R^2$ represents hydrogen or a $C_1$-$C_3$ alkyl, $R^3$ represents a $C_1$-$C_8$ alkyl, a $C_1$-$C_8$ alkenyl, a $C_1$-$C_8$ alkoxyalkyl, an acetooxy $C_1$-$C_3$ alkyl, or a $C_7$-$C_{15}$ arylalkyl, $R^4$ represents hydrogen or a $C_{1-4}$ alkyl, and $R^5$ represents hydrogen or a $C_{1-4}$ alkyl. In one form of this embodiment, the composition further includes an anionic compound having the following structure:

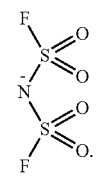

In another embodiment, an apparatus includes first and second substrates which are adhered together by a composition that includes a cationic compound according to Formula (I):

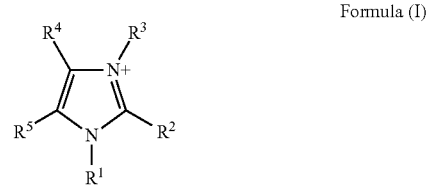

Formula (I)

wherein $R^1$ represents a $C_1$-$C_8$ alkyl, a $C_1$-$C_8$ alkenyl, or a $C_1$-$C_8$ alkoxyalkyl, $R^2$ represents hydrogen or a $C_1$-$C_3$ alkyl, $R^3$ represents a $C_1$-$C_8$ alkyl, a $C_1$-$C_8$ hydroxyalkyl, a $C_1$-$C_8$ alkenyl, a $C_1$-$C_8$ alkoxyalkyl, an acetooxy $C_1$-$C_3$ alkyl, or a $C_7$-$C_{15}$ arylalkyl, $R^4$ represents hydrogen or a $C_{1-4}$ alkyl, and $R^5$ represents hydrogen or a $C_{1-4}$ alkyl.

In another embodiment, a method involves adhering a first substrate to a second substrate with a composition that includes a cationic compound according to Formula (I):

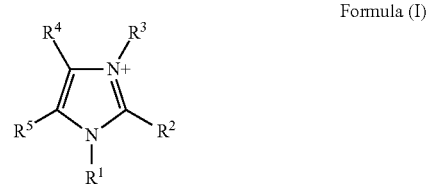

Formula (I)

wherein $R^1$ represents a $C_1$-$C_8$ alkyl, a $C_1$-$C_8$ alkenyl, or a $C_1$-$C_8$ alkoxyalkyl, $R^2$ represents hydrogen or a $C_1$-$C_3$ alkyl, $R^3$ represents a $C_1$-$C_8$ alkyl, a $C_1$-$C_8$ hydroxyalkyl, a $C_1$-$C_8$ alkenyl, a $C_1$-$C_8$ alkoxyalkyl, an acetooxy $C_1$-$C_3$ alkyl, or a $C_7$-$C_{15}$ arylalkyl, $R^4$ represents hydrogen or a $C_{1-4}$ alkyl, and $R^5$ represents hydrogen or a $C_{1-4}$ alkyl.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages will be set forth in the description which follows, and in part will be obvious from the description, or may be learned by practice. The features and advantages may be realized and obtained by means of the instruments and combinations particularly pointed out in the appended claims. These and other features will become more fully apparent from the following description and appended claims.

DETAILED DESCRIPTION

Figure 1:
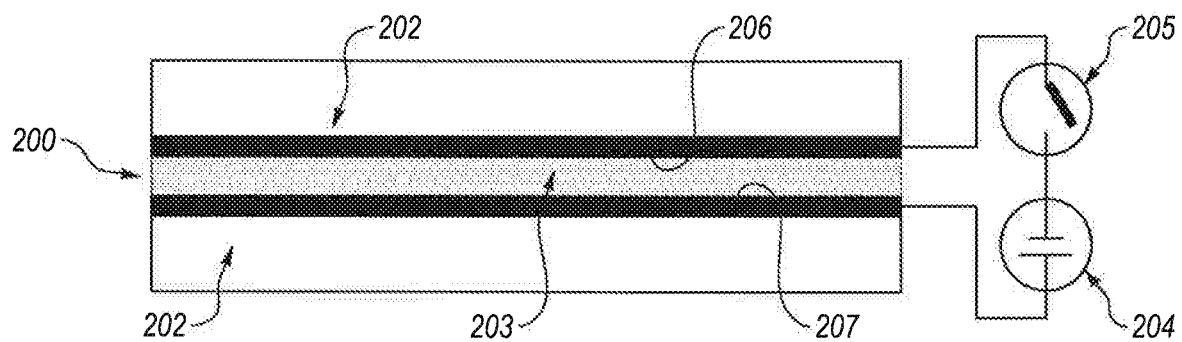
FIG. 1 is a schematic illustration of the use of an ionic composition described herein for adhering two substrates together.

For purposes of promoting an understanding of the present disclosure, reference will now be made to the following embodiments and specific language will be used to describe the same. It will nevertheless be understood that no limitation of the scope of the disclosure is thereby intended, such alterations and further modifications in the described subject matter, and such further applications of the disclosed principles as described herein being contemplated as would normally occur to one skilled in the art to which the disclosure relates.

The present disclosure generally relates to ionic compositions which may be used in or as an adhesive material for selectively adhering two items together. More particularly, but not exclusively, the present disclosure relates to ionic compositions that include a cationic imidazolium compound and an anionic compound such as a sulfonyl imide compound.

As used herein, when a compound or chemical structural is referred to as being "optionally substituted" it includes a feature that has no substituents (i.e. unsubstituted), or a feature that is "substituted," meaning that the feature has one or more substituents. A substituted group is derived from the unsubstituted parent structure wherein one or more hydrogen atoms on the parent structure have been independently replaced by one or more substituent groups. A substituted group may have one or more substituent groups on the parent group structure. In one or more forms, the substituent groups may be independently selected from optionally substituted alkyl or alkenyl, alkoxy (e.g. —$OCH_3$, —$OC_2H_5$, —$OC_3H_7$, —$OC_4H_9$, etc.), alkylsulfones (e.g. —$SCH_3$, —$SC_2H_5$, —$SC_3H_7$, —$SC_4H_9$, etc.), —NR'R", —OH, —SH, —CN, —$NO_2$, or a halogen, wherein R' and R" are independently H or an optionally substituted alkyl.

As used herein, the term "imidazolium" refers to the ring system having the following structure:

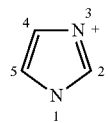

As used herein, the terms "bis(sulfonyl)imide" and/or "sulfonyl imide" refer to a heteroatom moiety having, for example, the following structure:

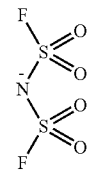

In one embodiment, an ionic composition includes a cationic imidazolium compound according to Formula (I):

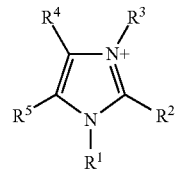

Formula (I)

wherein $R^1$ may represent a $C_1$-$C_8$ alkyl, a $C_1$-$C_8$ alkenyl, or a $C_1$-$C_8$ alkoxyalkyl; $R^2$ may represent hydrogen or a $C_1$-$C_3$ alkyl; $R^3$ may represent a $C_1$-$C_8$ alkyl, a $C_1$-$C_8$ hydroxyalkyl, a $C_1$-$C_8$ alkenyl, a $C_1$-$C_8$ alkoxyalkyl, an acetooxy $C_1$-$C_3$ alkyl, or a $C_7$-$C_{15}$ arylalkyl; and $R^4$ and $R^5$ may independently represent hydrogen or a $C_{1-4}$ alkyl.

In some forms, one or more of $R^1$, $R^2$, $R^3$, $R^4$ and $R^5$ may represent a hydrophilic functional group. In a more particular form, one more of $R^1$, $R^2$, and $R^3$ may represent a hydrophilic functional group. In one or more of these forms, the hydrophilic functional group may include oxygen. In some forms, the oxygen containing hydrophilic functional group may include an ether, hydroxyl, alkoxy and/or ester group. In other forms, the hydrophilic functional group may include nitrogen, sulfur and/or phosphorous. In still other forms, the hydrophilic functional group may include an amino group, a sulfhydryl group or a phosphate group.

In one or more forms, one or more of $R^1$, $R^2$, $R^3$, $R^4$ and $R^5$ may represent a hydrophobic functional group. In a more particular form, one or more of $R^1$, $R^2$, and $R^3$ may represent a hydrophobic functional group. In one or more of these forms, the hydrophobic functional group may include an optionally substituted alkyl group. In some forms, the optionally substituted alkyl group may include a methyl, ethyl, and/or propyl group. In other forms, the hydrophobic functional group[s] may include an optionally substituted aryl group. In some forms, the optionally substituted aryl group may include a phenyl and/or benzyl group.

In one or more forms, one or more of $R^1$, $R^2$, $R^3$, $R^4$ and $R^5$ may be independently substituted, and the cationic compound according to Formula (I) may be asymmetrical.

As indicated above, $R^1$ may represent a $C_1$-$C_8$ alkyl, a $C_1$-$C_8$ alkenyl, or a $C_1$-$C_8$ alkoxyalkyl. In some more particular forms, $R^1$ may represent a $C_1$-$C_3$ alkyl or a $C_1$-$C_3$ alkoxyalkyl. In one or more of these forms, the $C_1$-$C_3$ alkyl may be a methyl, ethyl, n-propyl, or isopropyl group. In some forms, the $C_1$-$C_8$ alkoxyalkyl may represent a methyloxymethyl group.

As indicated above, $R^2$ may represent hydrogen or a $C_1$-$C_3$ alkyl. In some more particular forms, $R^2$ may represent hydrogen. In some more particular forms, $R^2$ may represent a methyl or ethyl group.

As indicated above, $R^3$ may represent a $C_1$-$C_8$ alkyl, a $C_1$-$C_8$ hydroxyalkyl, a $C_1$-$C_8$ alkenyl, a $C_1$-$C_8$ alkoxyalkyl, an acetooxy $C_1$-$C_3$ alkyl, or a $C_7$-$C_{15}$ arylalkyl. In some more particular forms, $R^3$ may represent a $C_1$-$C_8$ alkyl, a $C_1$-$C_8$ alkenyl, or a $C_1$-$C_8$ alkoxyalkyl. In some other forms, $R^3$ may represent a $C_1$-$C_3$ alkyl, a $C_1$-$C_3$ alkoxy, a $C_1$-$C_3$ hydroxyalkyl such as —$CH_2CH_2$—OH, a $C_1$-$C_3$ alkoxy, an acetooxy $C_1$-$C_3$ alkyl, or a $C_5$-$C_7$ arylalkyl such as —$CH_2$-phenyl. In some forms, $R^3$ may represent a methyl or ethyl group. In other forms, $R^3$ may represent a $C_1$-$C_3$ alkoxy which may be, for example, a methoxy or ethoxy group. In some forms, $R^3$ may represent $C_1$-$C_3$ hydroxyalkyl such as —$CH_2CH_2$—OH. In some forms $R^3$ may represent a methyloxymethyl or ethoxymethyl group. In other forms, $R^3$ may represent an acetooxy $C_1$-$C_3$ alkyl which may be an acetoxyethyl group. In some forms, $R^3$ may represent a $C_5$-$C_7$ arylalkyl group which may be a benzyl group.

As indicated above, $R^4$ and $R^5$ may independently represent hydrogen or a $C_{1-4}$ alkyl. In one more particular form, at least one of $R^4$ and $R^5$ is a $C_{1-4}$ alkyl. In one particular form, $R^4$ represents a $C_1$-$C_2$ alkyl and $R^5$ represents hydrogen. In another form, $R^4$ represents hydrogen and $R^5$ represents a $C_1$-$C_2$ alkyl. In another form, $R^4$ represents methyl and $R^5$ represents hydrogen. In another form, $R^4$ represents hydrogen and $R^5$ represents methyl. In another form, one or both of $R^4$ and $R^5$ represent $C_1$-$C_2$ alkyls. In yet another form, one or both of $R^4$ and $R^5$ represent a $C_1$-$C_4$ alkyl. In still another form, $R^4$ represents a $C_1$-$C_2$ alkyl or a $C_1$-$C_4$ alkyl and $R^5$ represents hydrogen. In a further form, $R^5$ represents a $C_1$-$C_2$ alkyl or a $C_1$-$C_4$ alkyl and $R^4$ represents hydrogen. In another form, $R^4$ and $R^5$ both represent a $C_1$-$C_2$ alkyl which may be, for example, a methyl group and/or an ethyl group. In another form, $R^4$ and $R^5$ both represent $CH_3$.

Still, other variations for the cationic compound according to Formula (I) are possible. For example, in one form, $R^1$ may be selected from —H, —$CH_3$, —$CH_2$—$CH_3$, —$CH_2$—$(CH_3)_2$, and —$CH_2$—O—$CH_3$, $R^2$ may be selected from —H, —$CH_3$, and —$CH_2$—$CH_3$, $R^3$ may be selected from —H, —$CH_3$, —$CH_2$—$CH_3$, —$CH_2$—$(CH_3)_2$, —$CH_2$—O—$CH_3$, —$CH_2$—$CH_2$—OH, —$CH_2$—$CH_2$—O—$CH_3$,

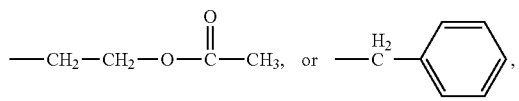

$R^4$ may be selected from —H, —$CH_3$, or —$CH_2$—$CH_3$, and/or $R^5$ may be selected from —H, —$CH_3$, and/or —$CH_2$—$CH_3$. As another example, in another form, $R^1$ may be selected from —$CH_3$, —$CH_2$—$CH_3$, —$CH_2$—$(CH_3)_2$, and —$CH_2$—O—$CH_3$, $R^2$ may be selected from —H, —$CH_3$, and —$CH_2$—$CH_3$, $R^3$ may be selected from —$CH_3$, —$CH_2$—$CH_3$, —$CH_2$—O—$CH_3$, —$CH_2$—$CH_2$—O—$CH_3$, or

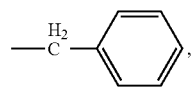

$R^1$ may be selected from —H or —$CH_3$, and/or $R^5$ may be selected from —H or —$CH_3$. In yet a further example, in another form, $R^1$ may be selected from —$CH_3$, —$CH_2$—$CH_3$, and —$CH_2$—$(CH_3)_2$, $R^2$ may be selected from —H, —$CH_3$, and —$CH_2$—$CH_3$, $R^3$ may be selected from —$CH_3$ and —$CH_2$—$CH_3$, $R^4$ may be selected from —H or —$CH_3$, and/or $R^5$ may be selected from —H or —$CH_3$.

Representative compounds according to Formula (I) include, but are not limited to, those presented in Table 1:

TABLE 1

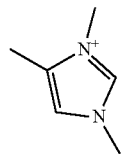

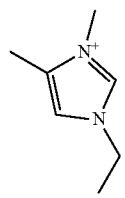

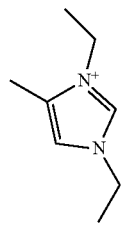

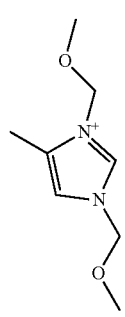

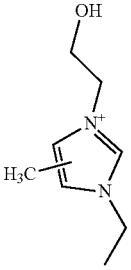

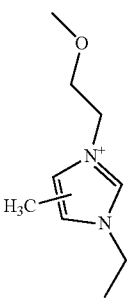

TABLE 1-continued
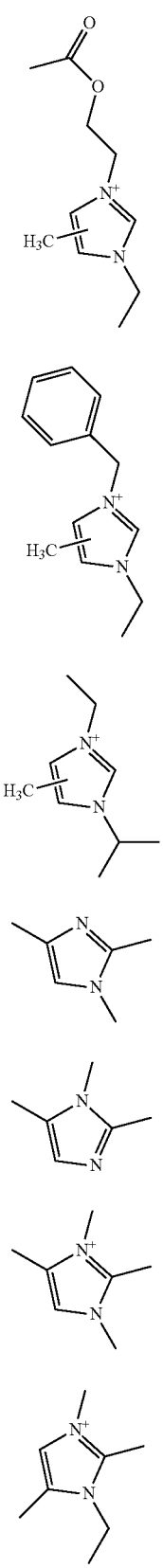
TABLE 1-continued
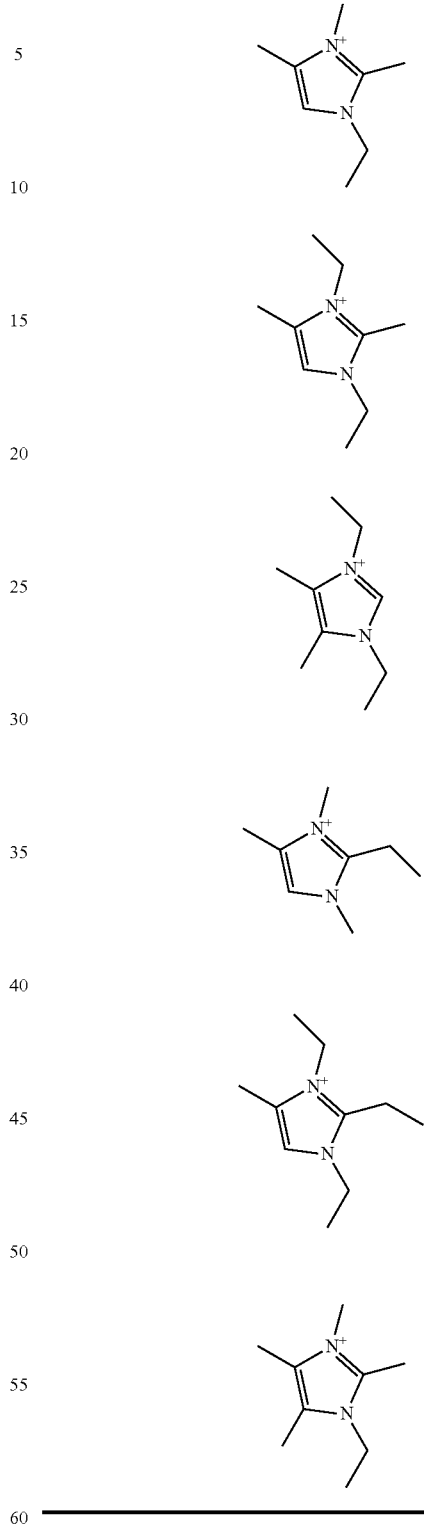
The ionic composition disclosed herein may also include an anionic compound. In one form, the anionic compound may be a bis(sulfonyl)imide anion. In a more particular form, the bis(sulfonyl)imide anion may be a bis(fluorosulfonyl)imide compound. In one form, the bis(fluorosulfonyl)imide compound may have the following structure:

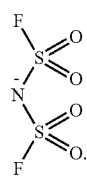

The ionic compositions described herein may be utilized as, or in, an adhesive material which may be used to bond two or more items together in a releasable fashion. Stated alternatively, the adhesive material may be used to selectively bond the items together, allowing for the adhesive material to be de-bonded from one or more of the items and facilitate separation of the items if desired. More particularly, an adhesive material according to the present disclosure may be provided on an electrically conductive surface of a first substrate, and an electrically conductive surface of a second substrate may be positioned in contact with the adhesive material in order to bond or join the first and second substrates together. In this configuration, the adhesive material is sandwiched between the first and second substrates, although other variations are contemplated. As indicated above, if desired, the adhesive material facilitates de-bonding and separation of the first and second substrates. More specifically, upon the application of an electric potential, the adhesive material will be de-bonded or released from the conductive surface of one or both of the substrates, resulting in separation of the first and second substrates from one another.

While not previously described, it should be appreciated that the compositions disclosed herein may include components in addition to the cationic and anionic compounds. For example, in one form, the compositions may also include a polymer. Non-limiting examples of polymers which could be present in the composition include those described in JP 2015-204998 and/or JP 2015-204996. In one form the polymer may have a glass transition temperature below 0° C., although other variations are possible. In one form, the polymer may be an acrylic polymer, such as but not limited to, an acrylic polymer which contains a monomer unit derived from a $C_1$-$C_{14}$ alkyl group containing alkyl (meth)acrylate ester. In other forms however, the acrylic polymer can contain a monomer unit derived from a $C_1$-$C_{14}$ alkyl or alkoxy group. In one form, the acrylic polymer may contain an alkyl (meth)acrylate ester, and a monomer unit derived from a polar group containing monomer. In one aspect of this form, the polar group containing monomer may be a carboxyl group containing monomer. In an additional or alternative aspect of this form, the $C_1$-$C_{14}$ alkyl group containing alkyl (meth)acrylate ester is butyl (meth)acrylate.

It is contemplated that the compositions described herein could be utilized for a number of different applications, including for example those disclosed in JP 2015-204996 and/or JP20204997.

Figure 2:
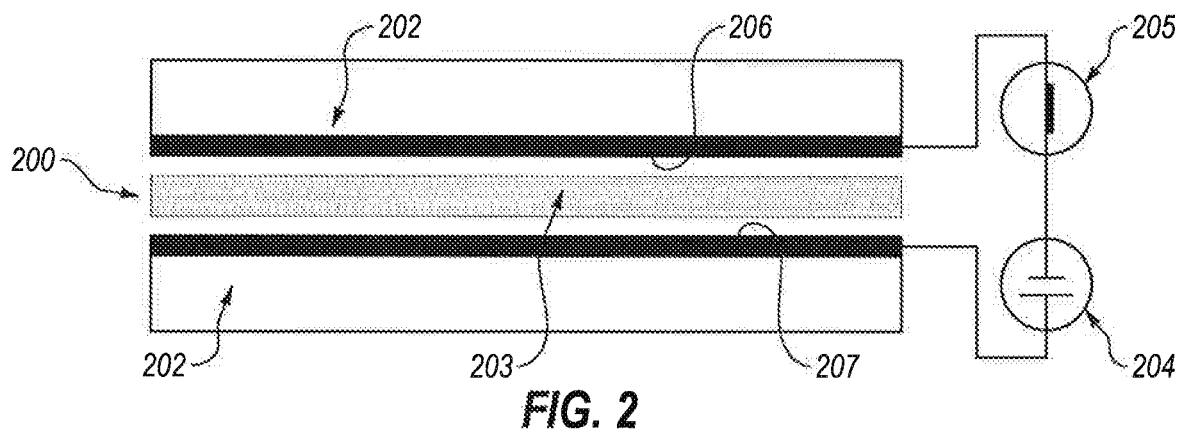
FIG. 2 is a schematic illustration of the release or debonding of the two substrates of FIG. 1 upon application of an electric potential.

Referring now to FIGS. 1 and 2, additional details regarding the use of an ionic composition described herein for selectively bonding two substrates together in apparatus 200 will be provided. An adhesive material 203 which includes an ionic composition described herein provides a layer or coating positioned between electrically conductive surface 206 of substrate 202 and electrically conductive surface 207 of substrate 201. In one form, one or both of substrates 201, 202 may be formed of an electrically conductive material such that one or both of electrically conductive surfaces 206, 207 is/are formed of the same material as the remainder of substrates 201, 202. However, it is possible in other forms to use one or more electrically conductive materials for electrically conductive surfaces 206, 207 which are different from the material(s) forming substrates 201, 202. Similarly, it should be appreciated that one or both of substrates 201, 202 could be formed of one or more materials which are not electrically conductive provided that surfaces 206, 207 are electrically conductive. In these forms, electrically conductive surfaces 206, 207 may be provided as a coating or layer on substrates 201, 202.

In the illustrated form, electrically conductive surfaces 206, 207 are electrically coupled to or in electrical communication with a power source 204 in a closeable electrical circuit that includes an intervening switch 205. In one form, power source 204 may be a direct current power supply that provides a DC voltage in the range of about 3V to 100V, although other variations are contemplated. When switch 205 is closed, the electrical potential is applied between electrically conductive surfaces 206, 207 in order to de-bond adhesive material 203 from one or both of electrically conductive surfaces 206, 207 and, as a result, allow substrates 201 and 202 to be physically separated from one another.

In one form, one or both of substrates 201, 202 may include an electrically conductive carbonaeceous material or an electrically conductive metal. As suggested above, one or both of substrates 201, 202 may also include an electrically conductive layer which may be formed of a metallic material such as, but not limited to, aluminum. The electrically conductive layer may include a conventional material such as a metal, mixed metal, alloy, metal oxide, and/or composite metal oxide, or it may include a conductive polymer. Examples of suitable metals for the electrically conductive layer include the Group 1 metals, the metals in Groups 4, 5, 6, and the Group 8-10 transition metals. Further examples of suitable metals for the electrically conductive layer include stainless steel, Al, Ag, Mg, Ca, Cu, Mg/Ag, LiF/Al, CsF, and/or CsF/Al and/or alloys thereof. If an electrically conductive layer is present, it may have a thickness in the range of about 1 nm to about 1000 μm. In one form, the electrically conductive layer has a thickness from about 20 nm to about 200 μm, and in another form the electrically conductive layer has a thickness in the range of about 20 nm to about 200 nm.

While not previously discussed, it should be appreciated that the ionic compositions described herein may provide various properties which are desirable for certain applications. For example, in some forms, the ionic compositions disclosed herein may eliminate or reduce corrosion of the electrically conductive surfaces on which they are positioned. In one form for example, the ionic compositions disclosed herein include components which reduce the acidity of the environment immediately adjacent to the electrically conductive surfaces. In one aspect, an adhesive material may include one or more materials, in addition to the cationic and anionic compounds themselves, which may be used to reduce the corrosiveness of the ionic cations and/or anions immediately adjacent the electrically conductive surfaces. The corrosive effect of an adhesive material may be assessed pursuant to the procedures described in ASTM G69-12 (Standard Test Method for Measurement of Corrosion Potentials of Aluminum Alloys). Additional procedures for assessing the corrosive effect of an adhesive material on the electrically conductive surfaces are described in the Examples of the subject application.

In one form, an adhesive material including an ionic composition disclosed herein may be chemically stable relative to an electrically conductive electrode or an electrically conductive material; i.e., there is a lack of (or minimal presence of) undesired reactions between a metal electrode and the adhesive material. Undesired reactions may include, for example, corrosive degradation of the metal electrode, dissolution of the metal in the selectively adherent adhesive and/or pitting of the metal electrode. An adhesive material including an ionic composition disclosed herein may be chemically stable relative to aluminum, stainless steel and/or mixtures thereof, just to provide a few examples. In one form, contact of an adhesive material including an ionic composition disclosed herein upon an electrically conductive surface may result in the absence of, or minimize, any corrosive degradation of the surface for a period of at least or greater than 15 minutes, 30 minutes, 1 hour, 3 hours, 5 hours, 7 hours, 24 hours, 50 hours, 100 hours, 125 hours, 200 hours and/or 300 hours. In some forms, direct contact of an adhesive material including an ionic composition disclosed herein upon an electrically conductive surface may minimize and/or prevent corrosive degradation of the surface for one of the time periods identified above in an environment of 85° C. and 85% relative humidity. In one form, the absence of any corrosive degradation can be demonstrated by a lack of total penetration of an electrically conductive 50 nm thick sheet of aluminum foil for one of the time periods identified above and/or at the environmental conditions identified above.

In one form, an adhesive material including an ionic composition described herein may be formulated to minimize corrosion of an electrically conductive surface under conditions of prolonged high humidity and high temperature. For example, an adhesive composition may be capable of maintaining two substrates in fixed relation to each other during and after being subjected to Accelerated Aging Test Method II (preferably after exposure to 85° C. and 85% relative humidity for one of the periods of time identified above). Also, while not previously discussed, it should be appreciated that the ionic compositions disclosed herein may have a molar mass that is less than or equal to about 160 grams per mole.

EXAMPLES

It should be appreciated that the following Examples are for illustration purposes and are not intended to be construed as limiting the subject matter disclosed in this document to only the embodiments disclosed in these examples.

Example 1: Preparation of
1,3,4-Trimethylimidazolium
bis(fluorosulfonyl)imide (68)

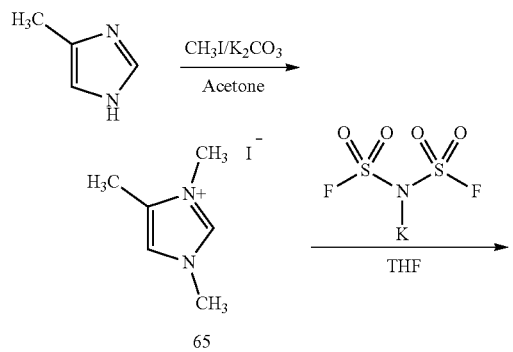

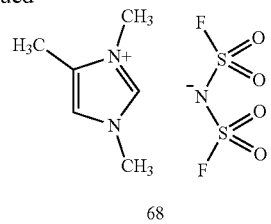

Iodomethane (62.2 mL, 1.0 mol) was added dropwise within 2 hours to a mixture of 4-methylimidazole (20.53 g, 250 mmol), potassium carbonate (41.40 g, 300 mmol), and acetone (300 mL) and stirred vigorously under argon. Heat from the reaction caused the temperature to rise to a boil. After the addition was complete, the mixture was stirred at 60° C. for 3 hours. The solid was filtered off from the hot reaction mixture and washed with boiling acetone (2×300 mL). The combined filtrate and washings were concentrated under reduced pressure and triturated with THF (500 mL) to give crystalline iodide product (65) (41.16 g, 69% yield).

A mixture of iodide (65) (9.52 g, 40 mmol), KFSI (8.76 g, 40 mmol) and THF (100 mL) was stirred under argon and heated at 70° C. for 4 hours. After cooling overnight, the solid was filtered off, and the solvent was removed under reduced pressure. A solution of the residue in ethyl acetate (100 mL) was washed with water (50 mL), filtered through a paper filter, and the solvent was removed under reduced pressure to give ionic liquid (68) (8.00 g, 69% yield). $^1$H NMR (400 MHz, DMSO-d$_6$): δ 8.93 (s, 1H), 7.42 (s, 1H), 3.79 (s, 3H), 3.73 (s, 3H), 2.26 (s, 3H).

Example 2: Preparation of
3,4-Dimethyl-1-ethylimidazolium
bis(fluorosulfonyl)imide (62)

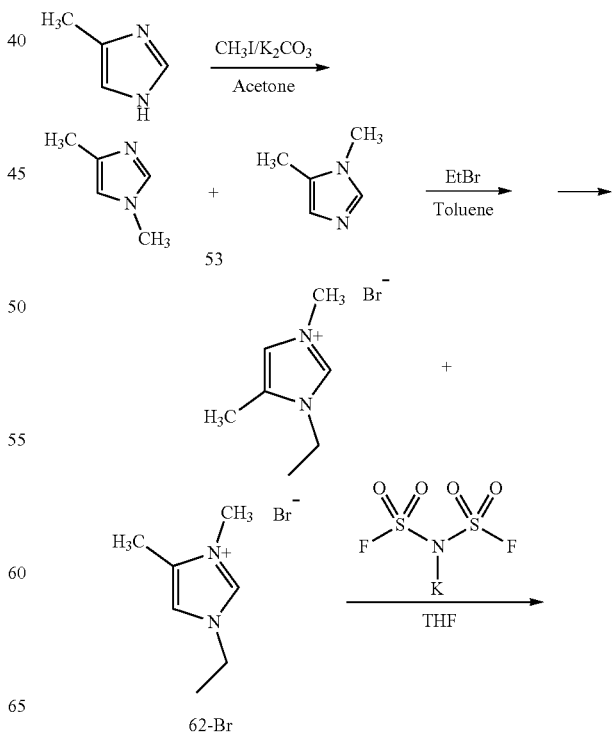

-continued

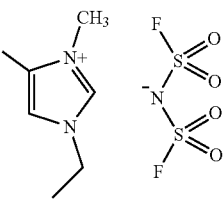

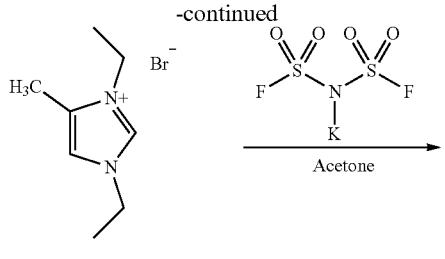

A solution of iodomethane (37.3 mL, 600 mmol) in acetone (40 mL) was added dropwise within 4 hours to a mixture of 4-methylimidazole (41.06 g, 500 mmol), potassium carbonate (103 g, 750 mmol) and acetone (500 mL). The mixture was then stirred at room temperature for 16 hours. The solid was filtered off, and the solvent was removed under reduced pressure. The residue was triturated with THF (200 mL) and set aside at room temperature overnight. The solid was removed by filtration and the solvent was evaporated under reduced pressure to give a mixture of isomers (53) (30.70 g), containing also some starting 4-methylimidazole.

A mixture of imidazoles (53) (30.00 g, 312 mmol), bromoethane (20 mL, 268 mmol) and toluene (50 mL) was placed in a pressure reactor and heated at 80° C. for 16 hours. The solvent was removed under reduced pressure. The residue was triturated with acetone (100 mL) and set aside at room temperature overnight. Obtained crystals were filtered off, washed with acetone and dried in a vacuum oven to give imidazolium bromide (62-Br) (6.43 g, 10% yield).

A mixture of imidazolium bromide (62-Br) (6.43 g, 30.7 mmol), KFSI (6.57 g, 30 mmol) and THF (100 mL) was stirred under argon and heated at 75° C. for 5 hours. After cooling to 50° C., the solid was filtered off, and the solvent was removed under reduced pressure to give ionic liquid (62) (8.61 g, 94% yield). $^1$H NMR (400 MHz, DMSO-d$_6$): δ 9.01 (s, 1H), 7.44 (s, 1H), 4.10 (q, J=7.3 Hz, 2H), 3.79 (s, 3H), 2.29 (s, 3H), 1.38 (t, J=7.3 Hz, 3H).

Example 3: Preparation of 1,3-Diethyl-4-methylimidazolium bis(fluorosulfonyl)imide (92)

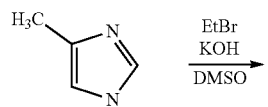

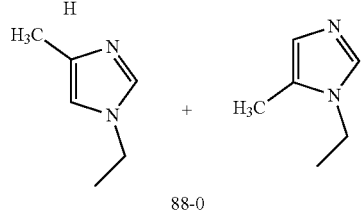

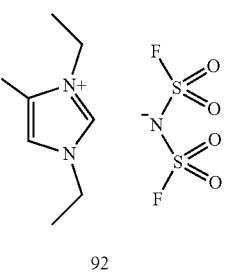

A mixture of 4-methylimidazole (39.80 g, 485 mmol), 90% KOH (31.10 g, 500 mmol) and anhydrous DMSO (150 mL) was stirred under argon for 3 hours. Bromoethane (37.2 mL, 500 mmol) was added dropwise while the reaction mixture was cooled in an ice-water bath. The mixture was then stirred at room temperature overnight. The reaction mixture was poured into ice-water (700 mL), treated with 5N NaOH (100 mL) and extracted with DCM/THF (9:1, 3×300 mL). The extract was washed with water (300 mL), dried over anhydrous sodium carbonate, and the solvent was removed under reduced pressure to give imidazoles (88-0) (41.97 g, 78% yield) as a mixture of two isomers in approximately equal amounts.

A mixture of imidazoles (88-0) (11.02 g, 100 mmol), bromoethane (11.2 mL, 150 mmol) and anhydrous toluene (50 mL) was sealed in a pressure reactor and heated at 80° C. for 16 hours. After cooling, the bottom phase was separated and triturated with ethyl ether (100 mL) to give a crystalline material. The product was recrystallized from acetone (100 mL) to give large shiny crystals of imidazolium bromide (88-Br) (13.83 g, 63% yield).

A mixture of imidazolium bromide (88-Br) (8.57 g, 39.1 mmol), KFSI (8.57 g, 39.1 mmol) and acetone (100 mL) was stirred under argon and heated at 60° C. for 2 hours. The solid was filtered off, and the solvent was removed under reduced pressure. A solution of the residue in THF (100 mL) was set aside at room temperature overnight, filtered to remove a small amount of additional precipitate, and the solvent was evaporated under reduced pressure to give 1,3-diethyl-4-methylimidazolium bis(fluorosulfonyl)imide (92) (12.48 g, 100% yield). $^1$H NMR (500 MHz, DMSO-d$_6$): δ 9.07 (s, 1H), 7.53 (s, 1H), 4.13 (q, J=7 Hz, 2H), 4.10 (q, J=7.0 Hz, 2H), 2.29 (s, 3H), 1.40 (m, 6H).

Example 4: Preparation of 1,3-Bis(methoxymethyl)-4-methylimidazolium bis(fluorosulfonyl)imide (46)

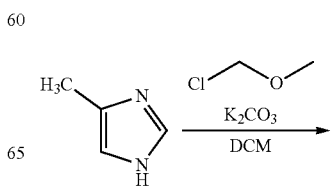

-continued

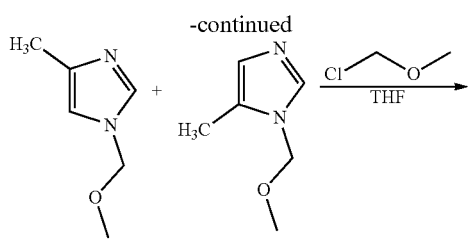

05

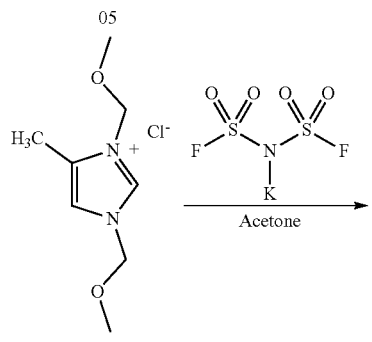

43

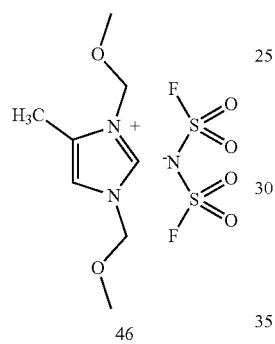

46

Chloromethyl methyl ether (51 mL, 634 mmol) was added dropwise within 3 hours to a vigorously stirred mixture of 4-methylimidazole (32.84 g, 400 mmol), potassium carbonate (89 g, 645 mmol) and DCM (200 mL). After addition, the mixture was stirred at room temperature overnight. The solid was filtered off and washed with acetone (300 mL). The combined filtrate and washings were concentrated under reduced pressure and the residue was chromatographed using silica gel and ethyl acetate/methanol (85:15) to give an isomeric mixture of mono-methoxymethylated imidazoles (05) (13.48 g, 27% yield).

Chloromethyl methyl ether (11.4 mL, 150 mmol) was added dropwise to a solution of imidazoles (05) (12.00 g, 95 mmol) in anhydrous THF (50 mL) and stirred under argon at room temperature. After the addition, stirring was continued for 5 hours. The mixture was divided into two layers. The bottom layer was separated, washed with ethyl ether (200 mL) and dissolved in methanol (200 mL). The dark solution was treated with charcoal (10 g) and stirred for 20 hours. The color turned yellowish. The solution was filtered through a layer of Celite, and the solvent was evaporated under reduced pressure to give imidazolium chloride (43) (17.69 g, 90% yield).

A mixture of imidazolium chloride (43) (9.92 g, 48 mmol), KFSI (10.52 g, 48 mmol) and acetone (100 mL) was stirred under argon at 60° C. for 1 hour. Charcoal (5 g) was added, and the mixture was stirred at room temperature for 2 hours. The solution was filtered through a layer of Celite, and the solvent was removed under reduced pressure to give ionic liquid (46) (15.46 g, 92% yield). $^1$H NMR (400 MHz, DMSO-$d_6$): δ 9.45 (s, 1H), 7.69 (s, 1H), 5.55 (s, 2H, N—$CH_2$—O), 5.51 (s, 2H, N—$CH_2$—O), 3.33 (s, 3H, $CH_3$O), 3.32 (s, 3H, $CH_3$O), 2.34 (s, 3H).

Example 5: Preparation of 1-Ethyl-3-(2-hydroxyethyl)-4(5)-methylimidazolium bis(fluorosulfonyl) imide (90)

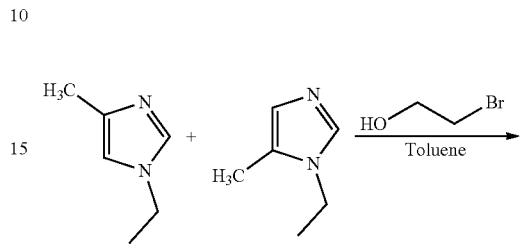

88-0

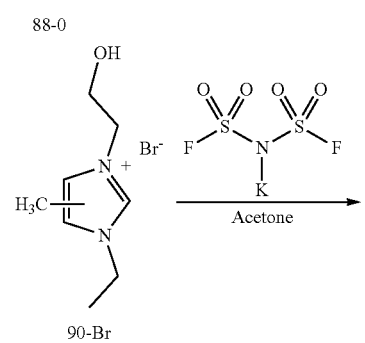

90-Br

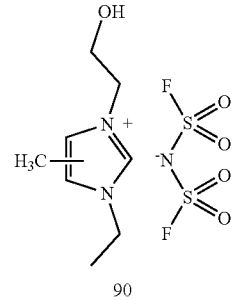

90

An isomeric mixture of imidazoles (88-0) (Example 3) (5.50 g, 50 mmol), 2-bromoethanol (5.3 mL, 75 mmol) and anhydrous toluene (25 mL) were sealed in a pressure reactor and heated at 100° C. for 16 hours. After cooling, the bottom phase was separated and triturated with ethyl ether (50 mL) to give an oily product. The oil was dried in a vacuum oven to give a mixture of isomers (90-Br) (11.57 g, 98% yield).

A mixture of isomers (90-Br) (9.87 g, 39.6 mmol), KFSI (8.68 g, 39.6 mmol) and acetone (100 mL) was stirred under argon and heated at 60° C. for 2 hours. The solid was filtered off, and the solvent was removed under reduced pressure. A solution of the residue in THF (100 mL) was set aside at room temperature overnight. It was then filtered to remove a small amount of additional precipitate, and the solvent was evaporated under reduced pressure to give a mixture of 1-ethyl-3-(2-methoxyethyl)-4-methylimidazolium bis(fluorosulfonyl)imide and its 5-methylimidazolium isomer (90) (7.64 g, 97% yield). $^1$H NMR of the major isomer (500 MHz, DMSO-$d_6$): δ 9.02 (s, 1H), 7.54 (s, 1H), 5.14 (bs, 1H, OH), 4.16 (m, 4H), 3.70 (m, 2H), 2.26 (s, 3H), 1.41 (t, J=7.5 Hz, 3H).

Example 6: Preparation of 1-Ethyl-3-(2-methoxyethyl)-4(5)-methylimidazolium bis(fluorosulfonyl)imide (91)

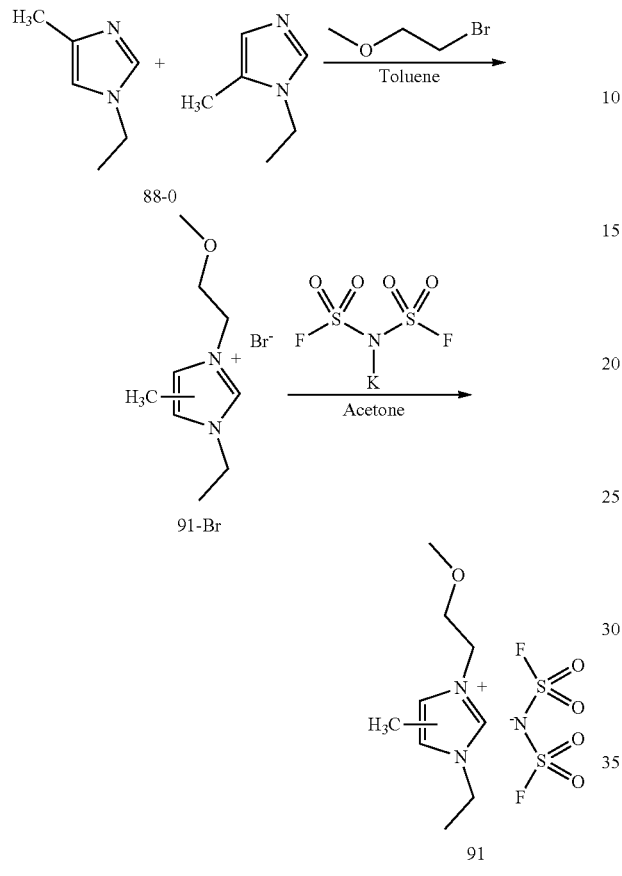

An isomeric mixture of imidazoles (88-0) (Example 3) (5.50 g, 50 mmol), 2-bromoethyl methyl ether (10.42 g, 75 mmol) and anhydrous toluene (25 mL) were sealed in a pressure reactor and heated at 80° C. for 16 hours. After cooling, the bottom phase was separated and triturated with ethyl ether (50 mL) to give an oily product. The oil was dried in a vacuum oven to give a mixture of isomers (91-Br) (9.87 g, 79% yield).

A mixture of isomers (91-Br) (9.87 g, 39.6 mmol), KFSI (8.68 g, 39.6 mmol) and acetone (100 mL) was stirred under argon and heated at 60° C. for 2 hours. The solid was filtered off, and the solvent was removed under reduced pressure. A solution of the residue in THF (100 mL) was set aside at room temperature overnight, filtered to remove a small amount of additional precipitate, and the solvent was evaporated under reduced pressure to give a mixture of 1-ethyl-3-(2-methoxyethyl)-4-methylimidazolium bis(fluorosulfonyl)imide and its 5-methylimidazolium isomer (91) (13.57 g, 98% yield), a mixture of two isomers in an approximate molar ratio of 55:45. $^1$H NMR of the major isomer (500 MHz, DMSO-$d_6$): δ 9.03 (s, 1H), 7.54 (s, 1H), 4.28 (t, J=5.0 Hz, 2H), 4.16 (q, J=7.5 Hz, 2H), 3.66 (t, J=4.5 Hz, 2H), 3.27 (s, 3H, MeO), 2.29 (s, 3H), 1.40 (t, J=7.5 Hz, 3H).

Example 7: Preparation of 1-Ethyl-3-(2-acetoxyethyl)-4(5)-methylimidazolium bis(fluorosulfonyl)imide (93)

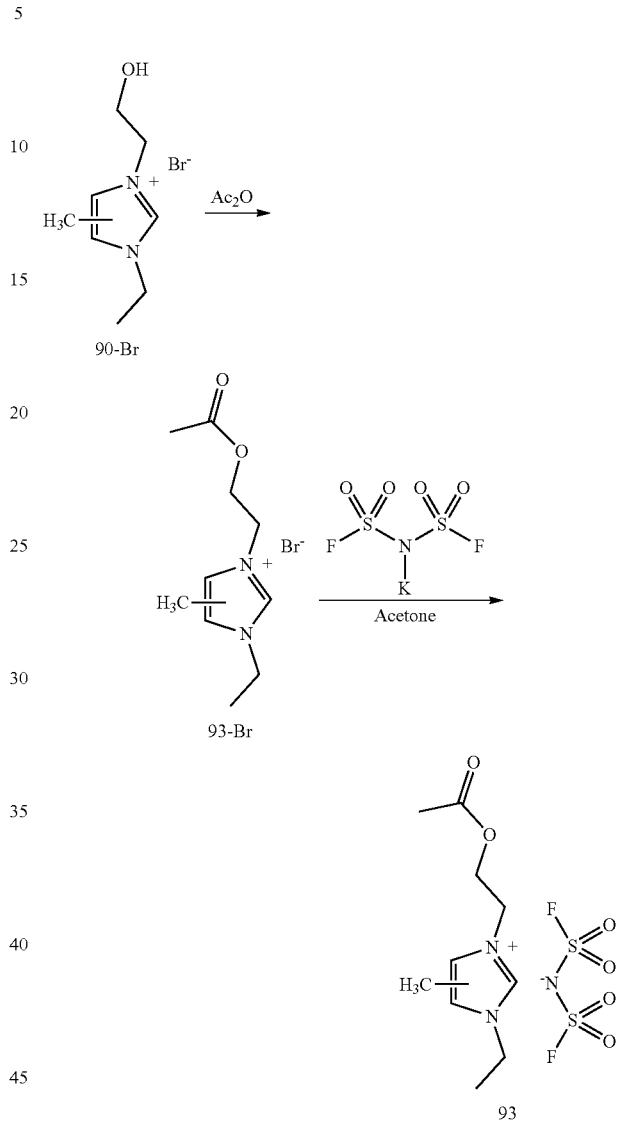

A mixture of imidazolium bromide (90-Br) (Example 5) (6.43 g, 27.3 mmol) and acetic anhydride (20 mL) was stirred under argon and heated at 100° C. for 6 hours. The mixture was diluted with m-xylene (100 mL) and concentrated under reduced pressure. Dilution with m-xylene and evaporation under reduced pressure was repeated to give product (93-Br) (7.20 g, 95% yield) as a mixture of two isomers in an approximately 1:1 ratio.

A mixture of product (93-Br) (7.00 g, 25.2 mmol), KFSI (5.54 g, 25.2 mmol) and acetone (100 mL) was stirred under argon and heated at 60° C. for 3 hours. After cooling, the solid was filtered off, and the solvent was removed under reduced pressure. A solution of the residue in anhydrous THF (75 mL) was set aside at room temperature overnight, then filtered and concentrated under reduced pressure to give ionic liquid (93).

Example 8: Preparation of 1-Ethyl-3-benzyl-4(5)-methylimidazolium bis(fluorosulfonyl)imide (94)

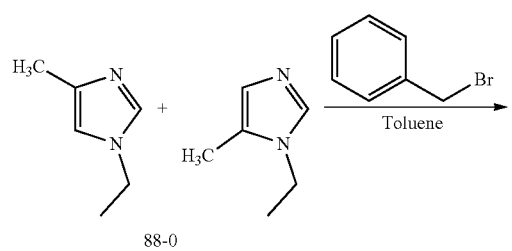

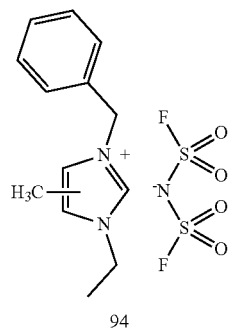

A mixture of imidazoles (88-0) (Example 3) (8.30 g, 75 mmol), benzyl bromide (11.2 mL, 100 mmol) and toluene (100 mL) was heated at 80° C. for 16 hours. After cooling, the bottom layer was separated by decantation, washed with toluene (50 mL), then washed with THF (100 mL) and dried in a vacuum oven to give bromide (94-Br) (20.85 g, 99% yield).

A mixture of bromide (94-Br) (6.70 g, 23.8 mmol), KFSI (5.22 g, 23.8 mmol) and acetone (100 mL) was stirred under argon and heated at 60° C. for 3 hours. After cooling, the solid was filtered off, and the solvent was evaporated under reduced pressure. The residue was dissolved in anhydrous THF, and set aside at room temperature for 4 hours. The solution was filtered, and the solvent was removed under reduced pressure to give ionic liquid (94) (8.59 g, 95% yield).

Example 9: Preparation of 3-Ethyl-1-isopropyl-4(5)-methylimidazolium bis(fluorosulfonyl)imide (86)

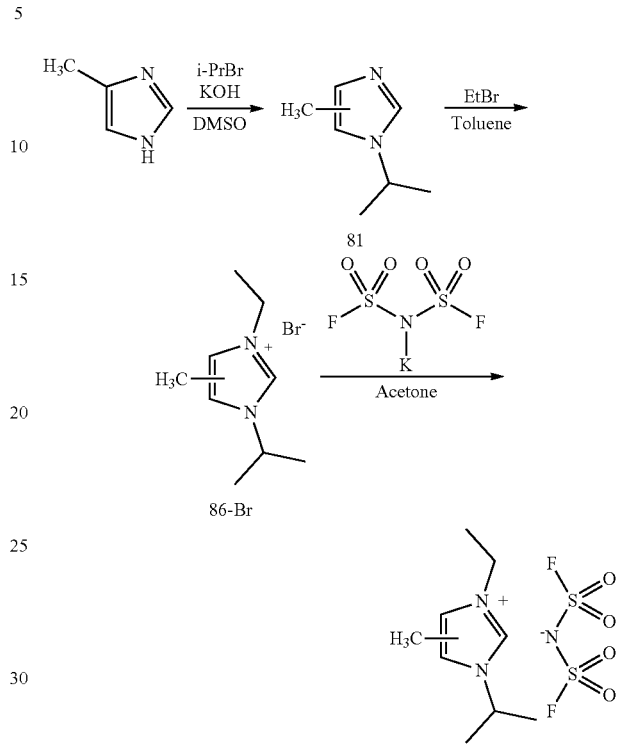

Potassium hydroxide (90%, 8.40 g, 134 mmol) was added to a solution of 4-methylimidazole in DMSO (100 mL), and the obtained mixture was stirred at room temperature for 1 hour. 2-Bromopropane (9.4 mL, 100 mmol) was then added dropwise while the mixture was cooled in an ice-water bath. After the addition, stirring at room temperature was continued overnight. The reaction mixture was poured into water (500 mL), treated with 5N NaOH (100 mL) and extracted with DCM (3×200 mL). The extract was washed with water (400 mL), dried over anhydrous sodium sulfate, and the solvent was removed under reduced pressure to give imidazole (81) (8.80 g, 71% yield) as a mixture of two isomers at a ratio of 2:1.

A mixture of imidazole (81) (8.50 g, 72 mmol), bromoethane (8 mL, 107 mmol) and toluene was sealed in a pressure reactor and heated at 80° C. for 16 hours. After cooling, the reactor was opened and the bottom layer was separated by decantation and triturated with ethyl ether to give a crystalline product. The product was recrystallized by dissolving it in hot THF/acetone (25+25 mL) and pouring the solution into cold THF (150 mL). After sitting overnight at room temperature, the snow-white crystals were filtered off, washed with THF (100 mL) and dried in a vacuum oven to give imidazolium bromide (86-Br) (14.62 g, 87% yield).

A mixture of imidazolium bromide (86-Br) (5.60 g, 24 mmol), KFSI (5.26 g, 24 mmol) and acetone (100 mL) was stirred under argon and heated at 60° C. for 3 hours. The solid was filtered off, and the solvent was removed under reduced pressure. A solution of the residue in THF (100 mL) was set aside at room temperature overnight, then filtered and concentrated under reduced pressure to give ionic liquid (86) (8.05 g, 100% yield), a mixture of two isomers in an approximate molar ratio of 2:1. $^1$H NMR of the major isomer (500 MHz, DMSO-$d_6$): δ 9.11 (s, 1H), 7.64 (s, 1H), 4.54 (m, 1H), 4.10 (q, J=7.5 Hz, 2H), 2.29 (s, 3H), 1.45 (d, J=7.0 Hz, 6H), 1.40 (t, J=7.5 Hz, 3H).

Example 10: Methylation of 2,4-dimethylimidazole

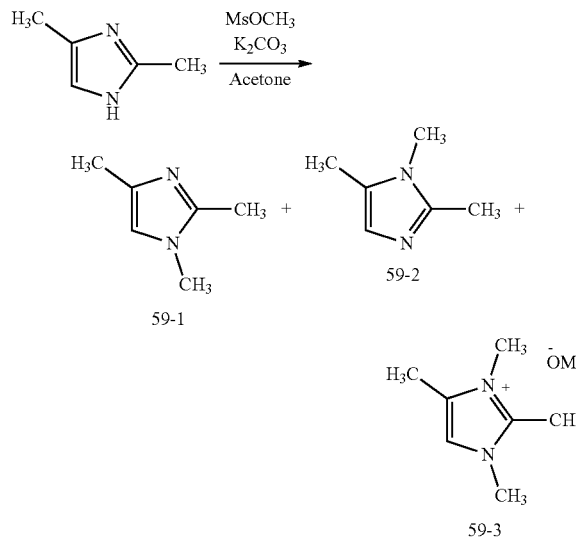

A solution of methyl mesylate (25.4 mL, 300 mmol) in acetone (50 mL) was added dropwise to a stirred mixture of 2,4-dimethylimidazole (25.00 g, 260 mmol), potassium carbonate (55.20 g, 400 mmol) and acetone (500 mL). Stirring under argon was then continued at room temperature for 16 hours. The resulting solid was filtered off, and the solvent was removed under reduced pressure. The residue was triturated with THF (200 mL) to give crystalline product (59-3) (14.47 g, 25% yield).

The filtrate was treated with activated charcoal, filtered through a layer of Celite, and the solvent was removed under reduced pressure. Upon storage of the residue at room temperature, some crystals were formed, and these crystals were separated, washed with THF and dried in a vacuum oven to give 1,2,4-trimethylimidazole (59-1) (4.01 g, 14% yield). Concentration of the filtrate gave a mixture of isomeric imidazoles (59-1) and (59-2) (12.19 g, 43% yield).

Example 11: Preparation of 1,2,3,4-tetramethylimidazolium bis(fluorosulfonyl)imide (64)

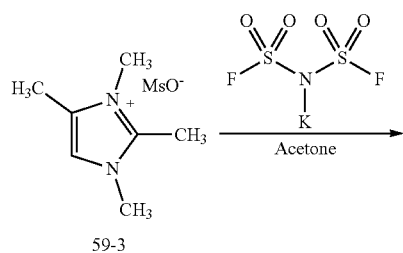

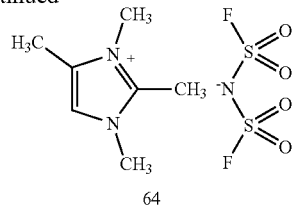

A mixture of mesylate (59-3) (Example 10) (14.47 g, 65.7 mmol), KFSI (13.59 g, 62 mmol) and acetone (100 mL) was stirred under argon and heated at 60° C. for 3 hours. After cooling, the mixture was diluted with THF (100 mL), the solid was filtered off, and the solvent was removed under reduced pressure to give salt (64) (17.01 g, 90% yield). $^1$H NMR (400 MHz, DMSO-$d_6$): δ 7.33 (s, 1H), 3.71 (s, 3H), 3.62 (s, 3H), 2.55 (s, 3H), 2.24 (s, 3H).

Example 12: Preparation of 3-Ethyl-1,2,4-trimethylimidazolium bis(fluorosulfonyl)imide (60)

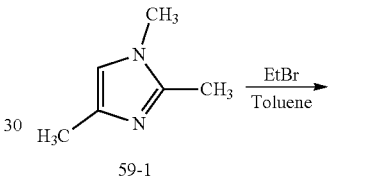

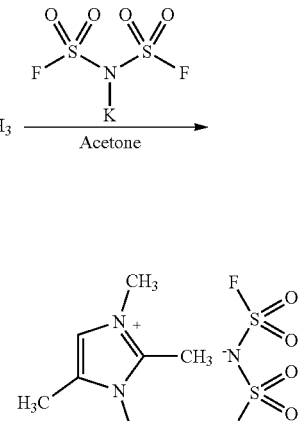

A mixture of imidazole (59-1) (Example 10) (4.00 g, 36.3 mmol), bromoethane (3.7 mL, 50 mmol) and toluene (20 mL) was sealed in a pressure reactor and heated at 80° C. for 3 days and nights. After cooling, the mixture was diluted with THF (20 mL). The solid was filtered off, washed with THF (20 mL) and dried in a vacuum oven to give bromide (60-Br) (7.46 g, 94% yield).

A mixture of (60-Br) (7.46 g, 34 mmol), KFSI (7.43 g, 34 mmol) and acetone (100 mL) was stirred under argon and heated at 50° C. for 16 hours. After cooling to room temperature, the solid was filtered off. The filtrate was concentrated under reduced pressure to give ionic liquid (60) (11.00 g, 100% yield). $^1$H NMR (500 MHz, DMSO-$d_6$): δ 7.33 (s, 1H), 4.10 (q, J=7.5 Hz, 2H), 3.69 (s, 3H), 2.61 (s, 3H), 2.27 (s, 3H), 1.26 (t, J=7.5 Hz, 3H).

Example 13: Preparation of 1-Ethyl-2,3,4-trimethylimidazolium bis(fluorosulfonyl)imide (61)

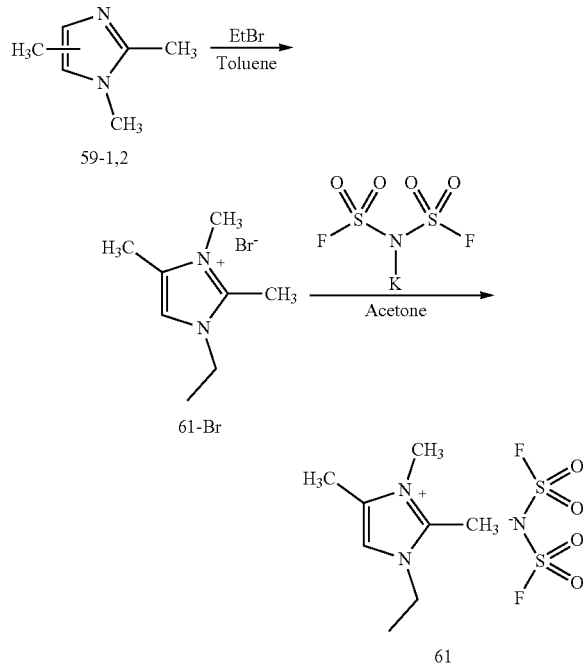

A mixture of imidazoles (59-1 and 59-2) (Example 10) (12.00 g, 109 mmol), bromoethane (11.2 mL, 150 mmol) and toluene was stirred under argon and heated at 60° C. for 4 hours. After cooling, the obtained solid was filtered off, washed with THF and recrystallized from a mixture of acetonitrile and THF to give crystalline bromide (61-Br) (8.91 g, 37% yield).

A mixture of bromide (61-Br) (8.91 g, 40.6 mmol), KFSI (8.90 g, 40.6 mmol) and acetone (100 mL) was stirred under argon and heated at 60° C. for 3 hours. After cooling to room temperature, the solid was filtered off, and the solvent was removed under reduced pressure to give ionic liquid (61) (9.20 g, 71% yield). $^1$H NMR (500 MHz, DMSO-$d_6$): δ 7.41 (s, 1H), 4.16 (q, J=7.5 Hz, 2H), 3.61 (s, 3H), 2.58 (s, 3H), 2.25 (s, 3H), 1.32 (t, J=7.0 Hz, 3H).

Example 14: Preparation of 1,3-Diethyl-2,4-dimethylimidazolium bis(fluorosulfonyl)imide (89)

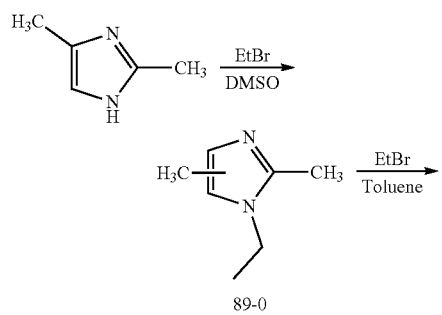

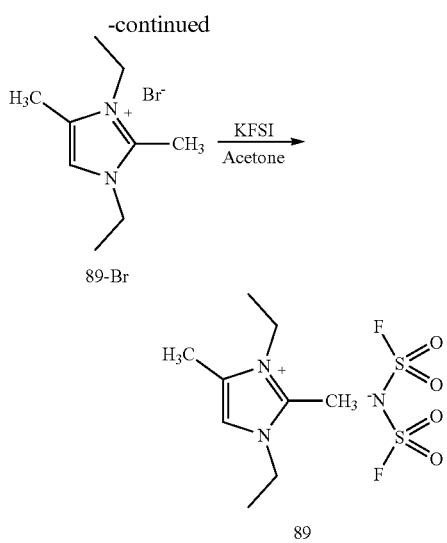

A mixture of 2,4-dimethylimidazole (19.23 g, 200 mmol), 90% KOH (15.60 g, 250 mmol) and anhydrous DMSO (100 mL) was stirred under argon at room temperature for 3 hours. Ethyl bromide (16.4 mL, 220 mmol) was added dropwise while the mixture was cooled in an ice-water bath. After stirring at room temperature overnight, the mixture was poured into ice-water (500 mL), treated with 5N NaOH (80 mL) and extracted with DCM/THF (9:1, 2×300 mL). The extract was dried over anhydrous $Na_2CO_3$, and the solvent was removed under reduced pressure to give a mixture of two isomeric mono-ethylated products (89-0) (22.49 g, 91% yield).

A mixture of imidazoles (89-0) (7.45 g, 60 mmol), bromoethane (7.46 mL, 100 mmol) and anhydrous toluene (50 mL) was sealed in a pressure reactor and heated at 50° C. for 3 days. The obtained crystals were separated, washed with ethyl ether and dried in a vacuum oven to give imidazolium bromide (89-Br) (11.08 g, 79% yield).

A mixture of imidazolium bromide (89-Br) (5.86 g, 25.1 mmol), KFSI (5.51 g, 25.1 mmol) and acetone (75 mL) was stirred under argon and heated at 60° for 2 hours. After cooling, the solid was filtered off, and the solvent was removed under reduced pressure. A solution of the residue in anhydrous THF (100 mL) was set aside at room temperature overnight, then it was filtered, and the solvent was removed under reduced pressure to give 1,3-diethyl-2,4-dimethylimidazolium bis(fluorosulfonyl)imide (89) (8.40 g, 100% yield). $^1$H NMR (500 MHz, DMSO-$d_6$): δ 7.43 (s, 1H), 4.10 (m, 4H), 2.61 (s, 3H), 2.28 (s, 3H), 1.33 (t, J=7.5 Hz, 3H), 1.27 (t, J=7.5 Hz, 3H).

Example 15: Preparation of 1,3-Diethyl-4,5-dimethylimidazolium bis(fluorosulfonyl)imide (87)

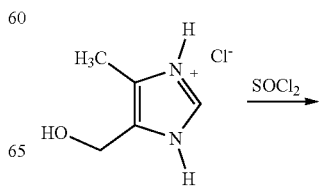

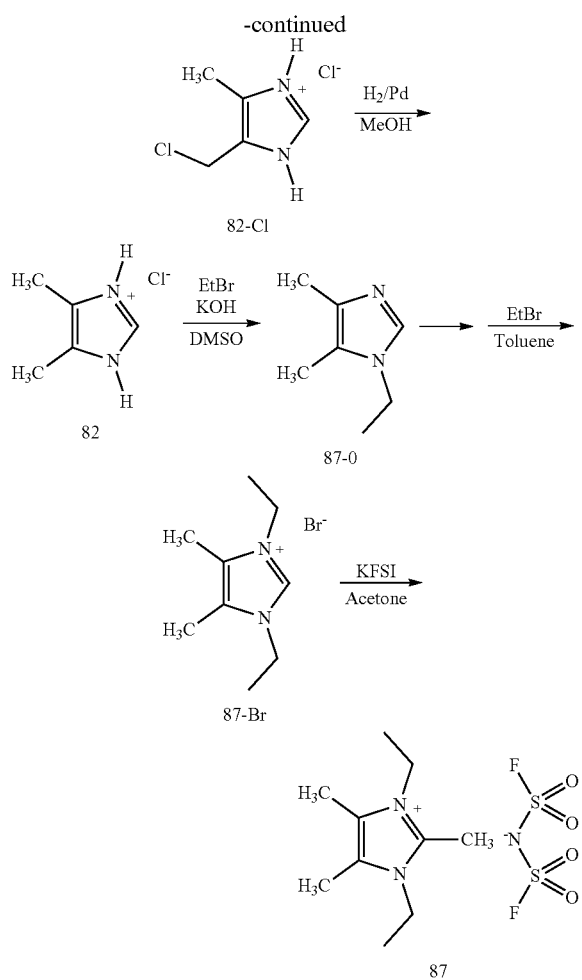

In a two neck flask equipped with a reflux condenser with an attached acid trap was placed 4-hydroxymethyl-5-methylimidazolium hydrochloride (10.00 g). Thionyl chloride (40 mL) was added in one portion causing the solid to dissolve, and new precipitation started to form within a couple of minutes. The mixture was heated then at 40° C. for 1 hour, diluted with ethyl ether (50 mL) and set aside at room temperature overnight. The solid was filtered off, washed with ethyl ether (2×50 mL) and dried in a vacuum oven to give imidazolium hydrochloride (82-Cl) (11.11 g).

A mixture of imidazolium hydrochloride (82-Cl) (11.00 g, 65.8 mmol), 10% Pd(C) (2 g) and methanol (200 mL) was hydrogenated at 60 psi of $H_2$ for 16 hours. The solid was filtered off using a Celite pad, and the solvent was removed under reduced pressure to give 4,5-dimethylimidazolium hydrochloride (82) (8.02 g, 92% yield).

A solution of 4,5-dimethylimidazolium hydrochloride (82) (8.00 g, 60.3 mmol) in anhydrous DMSO (100 mL) was treated with solid 90% KOH (11.20 g, 180 mmol) and bromoethane (4.9 mL, 65 mmol). The obtained mixture was stirred under argon and heated at 40° C. for 16 hours. The reaction mixture was poured into ice-water (500 mL), treated with 5N NaOH and extracted with DCM/THF (9:1, 2×200 mL). The extract was washed with water (100 mL), dried over $Na_2CO_3$, and the solvent was removed under reduced pressure to give 1-ethyl-4,5-dimethylimidazole (87-0) (5.43 g, 73% yield).

A mixture of 1-ethyl-4,5-dimethylimidazole (87-0) (5.40 g, 43.5 mmol), bromoethane (4.5 mL, 60 mmol) and toluene (30 mL) was placed in a pressure reactor and heated at 60° C. for 20 hours. After cooling, the bottom layer was separated by decantation and recrystallized from acetone (200 mL) to give imidazolium bromide (87-Br) (6.41 g, 63% yield).

A mixture of imidazolium bromide (87-Br) (6.38 g, 27.4 mmol), KFSI (6.00 g, 27.4 mmol) and acetone (100 mL) was stirred under argon and heated at 60° C. for 2 hours. After cooling to room temperature, the solid was filtered off, and the solvent was removed under reduced pressure. The residue was dissolved in THF (100 mL) and set aside at room temperature overnight. A small amount of solid was found on the flask bottom. The solution was filtered, and the solvent was removed under reduced pressure to give 1,3-diethyl-4,5-dimethylimidazolium bis(fluorosulfonyl)imide (87) (9.10 g, 99% yield). $^1$H NMR (500 MHz, DMSO-$d_6$): δ 9.01 (s, 1H), 4.09 (q, J=7.5 Hz, 4H), 2.24 (s, 6H), 1.38 (t, J=7.4 Hz, 6H).

Example 16: Preparation of 2-Ethyl-1,3,4-trimethylimidazolium bis(fluorosulfonyl)imide (75)

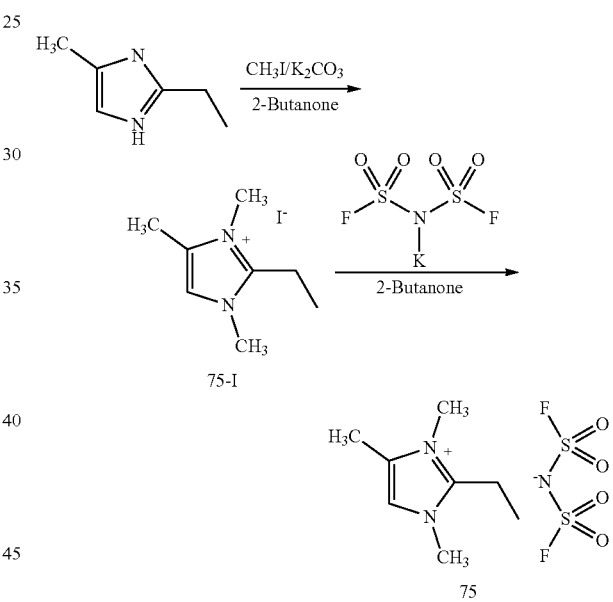

A solution of iodomethane (15.6 mL, 250 mmol) in 2-butanone (50 mL) was added dropwise to a suspension of potassium carbonate (41.40 g, 300 mmol) in a solution of 2-ethyl-4-methylimidazole (11.47 g, 100 mmol) in 2-butanone (50 mL) and stirred vigorously under argon. After the addition (3 hours), the mixture was heated under a reflux condenser at 60° C. for another 3 hours. The solid was filtered off from a warm reaction mixture and washed with 2-butanone (100 mL). Combined filtrate and washings were set aside at room temperature overnight to produce crystals of iodide (75-I), which were filtered off and dried in a vacuum oven. The second crop of iodide (75-I) was obtained by concentration of the filtrate. Washing of the potassium iodide solid with boiling 2-butanone (200 mL) produced two additional crops of iodide (754), total 12.89 g (48% yield).

A mixture of iodide (75-I) (6.34 g, 23.8 mmol), KFSI (5.22 g, 23.8 mmol) and 2-butanone (100 mL) was stirred under argon and heated at 60° C. for 4 hours. The solid was filtered off. The filtrate was diluted with ethyl acetate (400 mL), washed with 1% sodium thiosulfate (100 mL) followed by water (100 mL), dried over sodium sulfate, and the solvent was removed under reduced pressure to give ionic liquid (75). $^1$H NMR (500 MHz, DMSO-$d_6$): δ 7.33 (s, 1H), 3.74 (s, 3H), 3.66 (s, 3H), 3.30 (q, J=7.5 Hz, 2H), 2.24 (s, 3H), 1.16 (t, J=7.5 Hz, 3H).

Example 17: Preparation of 1,2,3-Triethyl-4-methylimidazolium bis(fluorosulfonyl)imide (84)

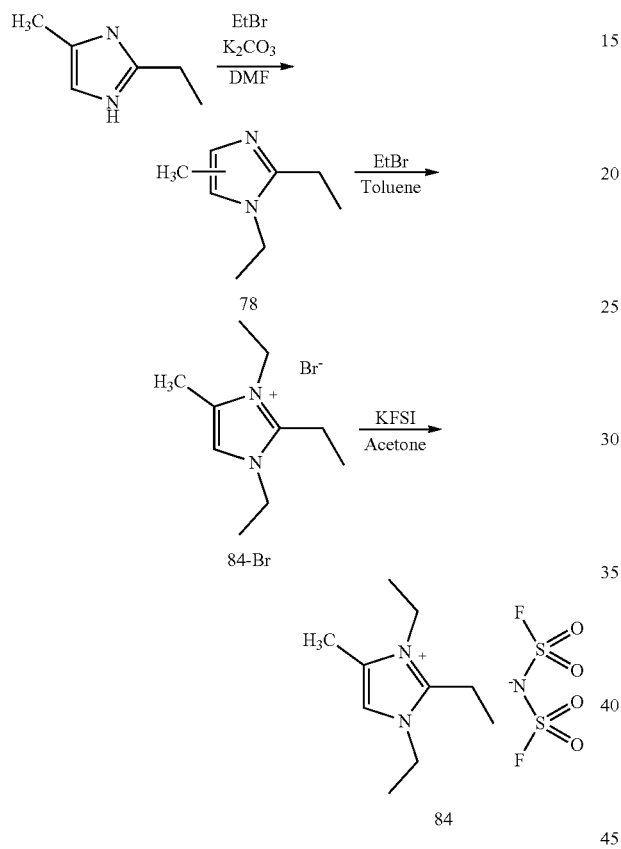

A mixture of 2-ethyl-4-methylimidazole (11.02 g, 100 mmol), potassium carbonate (13.80 g, 100 mmol), bromoethane (11.2 mL, 150 mmol) and DMF (100 mL) was stirred under argon and heated at 50° C. for 40 hours. The mixture was diluted with ethyl acetate (400 mL), stirred for 15 min, and the solid was filtered off. The solution was washed with water (2×100 mL), dried over anhydrous sodium sulfate, and the solvent was removed under reduced pressure to give product (78) (2.62 g, 19% yield) as a mixture of two isomers.

A solution of imidazole (78) (2.60 g, 19.8 mmol) in dry toluene (20 mL) was treated with bromoethane (2 mL, 27 mmol), and the obtained mixture was heated in a pressure reactor at 80° C. for 20 hours. After cooling to room temperature, the reactor was opened and the obtained crystals were filtered off, washed with toluene and dried in a vacuum oven to give imidazolium bromide (84-Br) (3.11 g, 64% yield).

A mixture of imidazolium bromide (84-Br) (3.10 g, 12.5 mmol), KFSI (2.75 g, 12.5 mmol) and acetone (75 mL) was stirred under argon and heated at 60° C. for 2 hours. After cooling, the solid was filtered off, and the solvent was removed under reduced pressure. The residue was dissolved in dry THF, and the obtained solution was set aside at room temperature for 2 hours. A small amount of precipitation was observed on the flask bottom. The solution was filtered, and the solvent was evaporated under reduced pressure to give 1,2,3-triethyl-4-methylimidazolium bis(fluorosulfonyl) imide (84) (4.38 g, 100% yield). $^1$H NMR (500 MHz, DMSO-$d_6$): δ 7.49 (s, 1H), 4.13 (m, 4H), 3.03 (q, J=7.5 Hz, 2H), 2.29 (s, 3H), 1.37 (t, J=7.5 Hz, 3H), 1.30 (t, J=7.5 Hz, 3H), 1.19 (t, J=7.5 Hz, 3H).

Example 18: Preparation of 1-Ethyl-2,3,4,5-tetramethylimidazolium bis(fluorosulfonyl)imide (57)

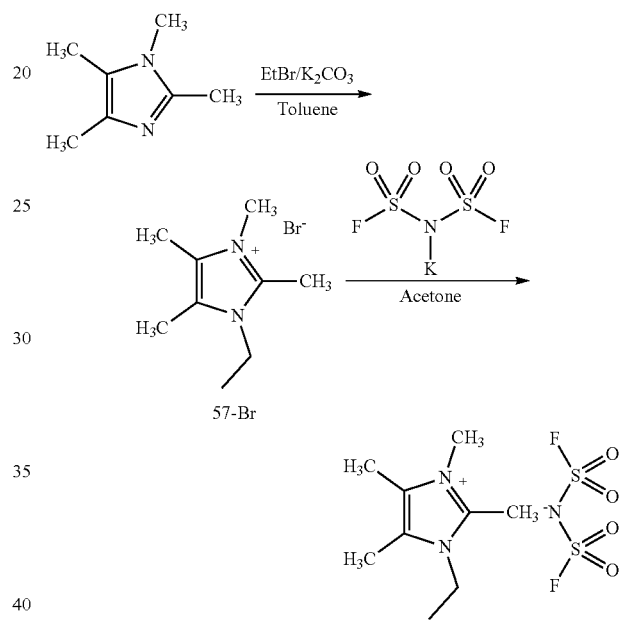

A mixture of 1,2,4,5-tetramethylimidazole (12.42 g, 100 mmol), bromoethane (11.2 mL, 150 mmol) and toluene (50 mL) was sealed in a pressure reactor and heated at 60° C. for 2 hours, then at 80° C. for 2 hours, and finally at 100° C. for 16 hours. After cooling, the solid was filtered off, washed with THF and recrystallized from acetonitrile/acetone to give product (57-Br) (13.70 g, 59% yield).

A mixture of product (57-Br) (13.70 g, 59 mmol), KFSI (12.06 g, 55 mmol) and acetone (100 mL) was stirred under argon and heated at 60° C. for 3 hours. After cooling, the solid was filtered off, and the solvent was removed under reduced pressure to give ionic liquid (57) (19.50 g, 58% yield). $^1$H NMR (400 MHz, DMSO-$d_6$): δ 4.10 (q, J=7.3 Hz, 2H), 3.60 (s, 3H), 2.60 (s, 3H), 2.24 (s, 3H), 2.21 (s, 3H).

Example 19: Corrosion Testing

Using a micropipette set at 5 µl, first and second aliquot samples of reference CE-1 (1-ethyl-3-methyl-imidazolium, Sigma Aldrich, St. Louis, MO) and first and second aliquot samples of the respective experimental Examples identified in Table 2 were placed in spaced apart arrangement on a 50 nm aluminum film (Toray Advanced Film, Tokyo, Japan). The prepared film was placed in a Temperature & Humidity Benchtop chamber, set at 85° C. and 85% Relative Humidity (RH) (ESPEC North America, Hudsonville, MI, USA, Criterion Temperature & Humidity Benchtop Model BTL-433) and was periodically checked at selected times (initially hourly). Either a colored sheet of paper and/or a light source was placed behind the prepared film and visually examined for an indication of total perforation at the spot of each aliquot deposit. If total perforation was observed, the time was recorded and the sample was indicated as a corrosive item. The results are shown in Table 2, below.

TABLE 2

| Composition | Time to Film Perforation (hours) |
|---|---|
| Reference Composition CE-1 | >120 |
| Example 1 Composition (68) | >125 |
| Example 2 Composition (62) | >200 |
| Example 3 Composition (92) | <3 |
| Example 4 Composition (46) | <1 |
| Example 13 Composition (61) | >200 |
| Example 16 Composition (75) | <3 |

Example 20: Preparation of Polymer Solution 95 mass parts of n-butyl acrylate, 5 mass parts of acrylic acid and 125 mass parts of ethyl acetate were introduced into a stirring flask attached to a condenser that was equipped with a nitrogen gas inlet. The mixture was stirred at room temperature while introducing the nitrogen gas for about 1 hour to remove oxygen from the reaction system. 0.2 mass parts of azobisisobutyronitrile (AIBN) was added, which increased the temperature of the resulting mixture to about 63°±2° C., and mixed/stirred for about 5-6 hours for polymerization. After stopping the reaction, an acrylic polymer-containing solution resulted, having a solid content of about 30%. The apparent molecular weight of the polymer solution (P1) was determined to be about 800,000 and had a glass transition temperature of about −50° C.

Example 21: Preparation of Adhesive Sheet

An adhesive sheet was prepared by mixing the polymer solution described in Example 20 with each of the compositions identified in Table 3 to obtain electrically de-bondable adhesive compositions. The prepared compositions were coated/deposited upon a surface treated PET separator (release liner) (MR38, made by Mitsubishi Plastics, Japan), forming an adhesive composite layer at a thickness of about 150 μm. The coated film was then heat dried at 130° C. for about 3 minutes followed by aging at 50° C. for 24 hours to obtain an adhesive layer/sheet having a thickness about 50 μm to obtain an adhesive layer/sheet. A PET release liner was aligned with the coated film and then aged at 50° C. for about 24 hours to obtain an adhesive layer/sheet having a thickness of about 50 μm.

Example 22: Preparation of Adhesive/Glass Substrate Test Samples

A commercially available pre-cleaned glass slide (3×1 inches) was used as substrate for an adhesive coating or layer. The glass slide substrate was further cleaned with acetone (Sigma Aldrich, St. Louis, MO, USA) and isopropyl alcohol (Aldrich) and then dried. A suitable amount of ethyl acetate was added to adjust the viscosity of slurry and then the slurry was casted on a pre-cleaned glass substrate with a thickness adjustable blade coater (BYK Gardner film casting knife). The cast tape was then cured at 130° C. for about 3 minutes in a preheated oven resulting in a dried coating over the substrate. A PET release liner was aligned with the coated glass and applied to the cured adhesive coated glass substrate. The release liner layered adhesive coated glass substrate was then aged/dried at about 50° C. for about 24 hours and stored under ambient conditions until needed.

Just prior to the application of the nano-Al coated layer, the aforementioned release liner was removed. The aluminum described previously above (50 nm-thick aluminum coated PET film (Toray Advanced Film) was applied to the adhesive coated surface of the glass substrate.

The prepared films were placed in a Temperature & Humidity Benchtop chamber, set at 85° C. and 85% Relative Humidity (ESPEC North America, Hudsonville, MI, USA, Criterion Temperature & Humidity Benchtop Model BTL-433) and were periodically checked at selected times (initially hourly). The interface between the adhesive and the aluminum foil was examined at regular predetermined time intervals, e.g., for an indication of corrosive degradation of the metal electrode, dissolution of the metal in the selectively adherent adhesive and/or pitting of the metal electrode. If corrosiveness was observed, the time was recorded and the sample was indicated as a corrosive item. The results are provided in Table 3 below.

TABLE 3

| Composition | Hours |
|---|---|
| No IL | <450 |
| 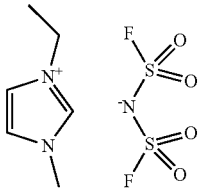 AS-110 Chemical Formula: $C_6H_{11}F_2N_3O_4S_2$ Molecular Weight: 291.29 | <325 |
| Example 2 Composition (62) | <200 |
| Example 3 Composition (92) | <325 |
| Example 17 Composition (84) | >450 |
| Example 9 Composition (86) | >450 |
| Example 15 Composition (87) | >450 |
| Example 14 Composition (89) | <200 |
| Example 8 Composition (94) | <325 |

Example 23: Electrical De-bonding of Adhesive Composition Testing

Figure 3:
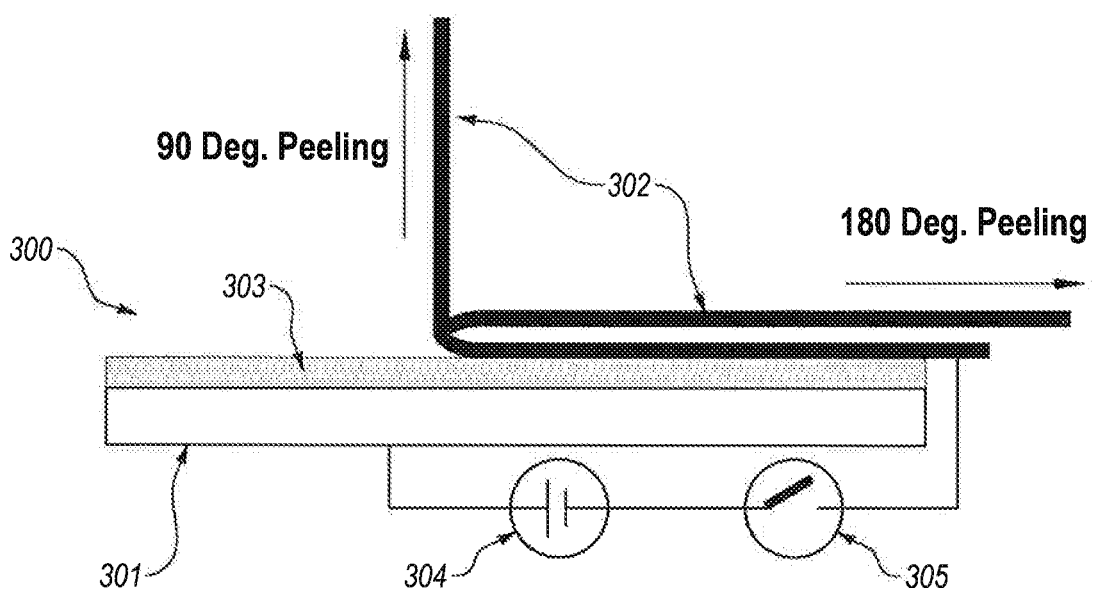
FIG. 3 is a schematic illustration of an apparatus used for testing adhesion properties of an ionic composition described herein.

Testing for electrical de-bonding or release of an adhesive composition was done in the manner as described in JP 2015-228951 and/or JP 2015-204998, and also shown in apparatus 300 of FIG. 3.

As shown in FIG. 3, adhesive material 303 (including composition (87) of Example 15) was coated upon a conductive substrate 301 which was 25 mm wide and 100 mm long. The resulting substrate 301 was laminated upon another flexible conductive layer 302 (such as aluminum foil and/or a metalized plastic film such as PET), which was 10 mm to 25 mm wide and 100 mm longer than substrate 301. The lamination was conducted by the application of rolling pressure by a 2 kg roller and roll press.

The bonding/de-bonding tester (Mark-10, Copiague, New York, USA, model ESM303 motorized tension/compression stand) was equipped with a Mark-10 force gauge (Series 7-1000) and had lower and upper clamps. The conductive substrate 301 was fixed onto the lower clamp and then electrically connected to the positive pole of a power supply 304 (Protek DC Power Supply 3006B). Flexible conductive layer 302 was fixed to the upper clamp which was connected with the negative pole of the same DC power supply. The power supply had an output range from 0 to 100 VDC. The moving/peeling speed was set at 300 mm/min. A switch 305 is present and, when closed, the electrical potential is applied between substrate 301 and layer 302.

Figure 4:
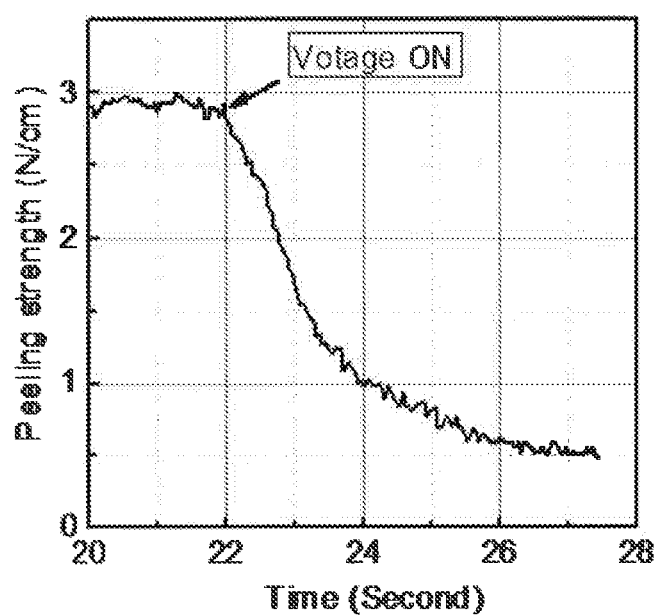
FIG. 4 is a graphical illustration of peeling strength density vs. time of the ionic composition tested in connection with FIG. 3.

In a dynamic test, voltage was applied a few seconds after the peeling or separation starts and the time and peeling strength readings from the force gauge were recorded by the data acquisition system (Mark-10 MESURgauge Plus). FIG. 4 shows the 180 degree peeling strength evolution with time when a 10 VDC was applied to the adhesive material that is doped with composition (87) of Example 15 at a concentration of 5 wt. %.

In a static de-bonding test, the sample was fixed on to the tester and connected to the power supply in the same way. The initial 180 degree peeling was measured at the same peeling speed. Then peeling was stopped. A DC voltage (10 VDC for example) was applied for some time (10 second for example). The peeling strength was then measured at the same peeling speed of 300 mm/min. For the same adhesive sample including composition (87) of Example 15, the initial peeling strength was 3.0 N/cm, and the residual adhesion peeling strength was ~0.5 after applying 10 VDC for 10 second.

For the processes and/or methods disclosed, the functions performed in the processes and methods may be implemented in differing order, as may be indicated by context. Furthermore, the outlined steps and operations are only provided as examples, and some of the steps and operations may be optional, combined into fewer steps and operations, or expanded into additional steps and operations.

This disclosure may sometimes illustrate different components contained within, or connected with, different other components. Such depicted architectures are merely exemplary, and many other architectures can be implemented which achieve the same or similar functionality.

The terms used in this disclosure, and in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.). In addition, if a specific number of elements is introduced, this may be interpreted to mean at least the recited number, as may be indicated by context (e.g., the bare recitation of "two recitations," without other modifiers, means at least two recitations, or two or more recitations). As used in this disclosure, any disjunctive word and/or phrase presenting two or more alternative terms should be understood to contemplate the possibilities of including one of the terms, either of the terms, or both terms. For example, the phrase "A or B" will be understood to include the possibilities of "A" or "B" or "A and B."

The terms and words used are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

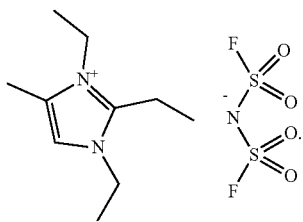

3. The adhesive composition of claim 1, wherein the ionic liquid is:
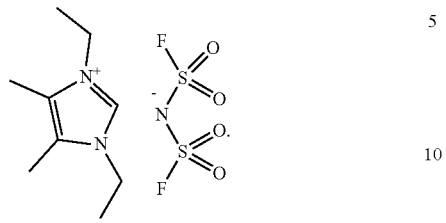

What is claimed is:

1. An adhesive composition, comprising an ionic liquid and a polymer, wherein the ionic liquid is

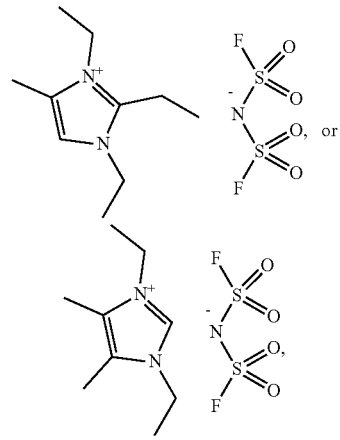

and wherein the polymer comprises monomers of n-butyl acrylate and acrylic acid.

2. The adhesive composition of claim 1, wherein the ionic liquid is: